United States Patent [19]
Goodson, Jr. et al.

[11] 3,962,214
[45] June 8, 1976

[54] PROCESS FOR PREPARING AMINO SUBSTITUTED β-LACTAM ANTIBIOTICS

[75] Inventors: Theodore Goodson, Jr.; Wayne A. Spitzer, both of Indianapolis, Ind.

[73] Assignee: Eli Lilly and Company, Indianapolis, Ind.

[22] Filed: July 11, 1974

[21] Appl. No.: 487,703

[52] U.S. Cl. .......................... 260/239.1; 260/243 C; 424/271; 424/246
[51] Int. Cl.² .............. C07D 499/04; C07D 501/02
[58] Field of Search ...................... 260/243 C, 239.1

[56] References Cited
FOREIGN PATENTS OR APPLICATIONS
3229   5/1971   South Africa ................... 260/243 C

*Primary Examiner*—Nicholas S. Rizzo
*Attorney, Agent, or Firm*—Walter E. Buting; Everet F. Smith

[57] ABSTRACT

6-Acylamino-6-alkylthiopenicillanic or 7-acylamino-7-alkylthiocephalosporanic acids or esters are reacted at a temperature between −80° and −25°C. with one equivalent of halogen to provide an intermediate halosulfonium halide which is reacted with a $C_1$–$C_4$ alkyl amine, a $C_1$–$C_4$ dialkylamine or ammonia in an appropriate solvent. The ester group is removed to provide the 6-aminopenicillanic or 7-aminocephalosporanic acid.

1 Claim, No Drawings

PROCESS FOR PREPARING AMINO SUBSTITUTED β-LACTAM ANTIBIOTICS

BACKGROUND OF THE INVENTION

Cephalosporin and penicillin antibiotics having various substituents attached to the $C_7$ and $C_6$ atoms of the β-lactam ring, respectively, are known. For example, 7-alkylthiocephalosporins and 6-alkylthiopenicillins are described by Spitzer and Goodson in Tet. Let. 273 (1973).

According to the method described therein, 7-acylamino-7-alkylthiocephalosporanic acids 7-acylamino-7-alkylthiodeacetoxycephalosporanic acids and 6-acylamino-6-alkylthiopenicillanic acids and esters thereof are prepared by reacting a benzylimine, prepared from a 6-aminopenicillin or a 7-aminocephalosporin compound and a substituted benzaldehyde with a strong base to generate the anion at $C_6$ of a penicillin or $C_7$ of a cephalosporin which is then treated with a thioalkylating agent.

SUMMARY OF THE INVENTION

A 6-acylamino-6-alkylthiopenicillin or a 7-acylamino-7-alkylthiocephalosporin is allowed to react with one equivalent of halogen in an inert solvent at a temperature between about −80° and about −25°C. to provide the corresponding halosulfonium halide. The halosulfonium group is displaced with a lower alkyl amine or ammonia to provide from the displacement a 6-alkylaminopenicillin or a 7-alkylaminocephalosporin.

The aminopenicillins and cephalosporins of this invention have useful antibiotic activity, and can be employed to combat infections caused by gram positive and gram negative microorganisms.

DETAIL DESCRIPTION

The present invention provides a process for the conversion of 6-alkylthio-6-acylaminopenicillins and 7-alkylthio-7-acylaminocephalosporins to the corresponding acylamino 6- and 7-amino, lower alkylamino, or di-lower alkylamino compounds. The conversion of the S-alkyl β-lactam compounds to the amino, alkylamino, and dialkylamino, compounds is carried out by reacting the S-alkyl compounds with halogen or a halogenating agent to provide the halosulfonium halide. For example, the chlorosulfonium chloride, formed in an appropriate inert solvent, is treated with ammonia, a lower alkyl amine or a lower dialkylamine to provide the amino compound.

According to the process of this invention a 6-acylamino-6-aminopenicillanic ester or a 7-acylamino-7-aminocephalosporanic ester represented by

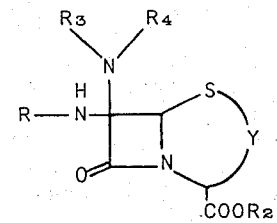

wherein R is an acyl group, $R_3$ and $R_4$ are the same or different, and represent $C_1$–$C_{14}$ alkyl or hydrogen, $R_2$ is hydrogen or a carboxylic acid ester forming group, and Y is

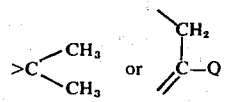

wherein Q is a methyl or acetoxymethyl group, is prepared from a 6-acylamino-6-alkylthiopenicillanic ester or a 7-acylamino-7-alkylthiocephalosporanic ester as represented in the equation

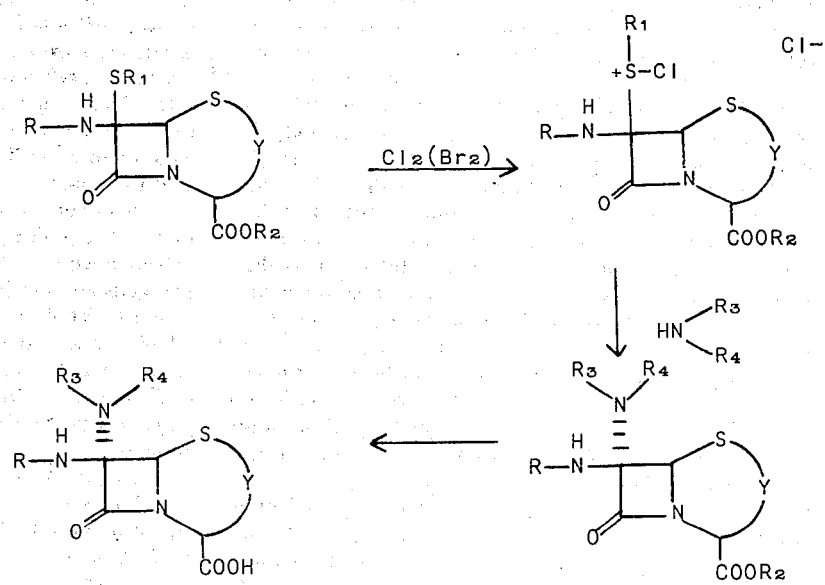

$R_1$ is $C_1$–$C_3$ alkyl or benzyl.

Though $R_2$ can be "a carboxylic acid protecting ester forming group" or hydrogen, yields are significantly greater if such an ester group is employed in the process.

The term "a carboxylic acid protecting ester forming group", as used herein, refers to such groups as are commonly employed in the penicillin and cephalosporin art to protect the respective carboxylic acid functions of the penicillin or cephalosporin molecule. Illustrative of such groups which can be used are the benzyl, 4-nitrobenzyl, 4 -methoxybenzyl, 3,5-dimethoxybenzyl, diphenylmethyl, 2,2,2-trichloroethyl, t-butyl, phenacyl, tetrahydropyranyl, and like carboxylic acid protecting groups. The nature of such ester forming groups is not critical in the present process except that such groups should preferably be less reactive toward halogenation than the 6- or 7-thioalkyl group. Such groups serve merely to protect the carboxylic acid function so as to prevent its competition with the chlorination and displacement reaction of the present process.

Conversion of the alkylthiopenicillin or alkylthiocephalosporin to the halosulfonium halide is carried out in an inert solvent at a temperature between about −80° and −25°C. with bromine, chlorine, or a source of halogen such as sulfuryl chloride to provide the halosulfonium halide. To the cold reaction mixture containing the halosulfonium halide is added an excess of an amine represented by the formula

wherein $R_3$ and $R_4$ are the same as above. The reaction product, a 6-acylamino-6-aminopenicillanic ester or a 7-acylamino-7-aminocephalosporanic ester is recovered from the reaction mixture.

In the foregoing description of this invention the term R represents an acyl group which can be any of a wide variety of acyl groups which have previously been described as the acyl moiety of the side chains of known penicillins and cephalosporins. For example, R can be a $C_1$–$C_7$ alkanoyl group such as acetyl, propionyl, valeryl, and the like; a $C_1$–$C_7$ haloalkanoyl group, for example, chloroacetyl, bromoacetyl, 2-chloropropionyl, and the like; a $C_7$–$C_{11}$ aroyl group, for example, benzoyl, α-naphthoyl; a mono- or di- substituted benzoyl, for example 2,6-dimethoxybenzoyl, 4-nitrobenzoyl, 4-methylbenzoyl, 4-hydroxybenzoyl, 4-nitrobenzoyl, 4-methylbenzoyl, 4-hydroxybenzoyl, 4-chlorobenzoyl, 3,4-dichlorobenzoyl, 4-bromobenzoyl, and the like; an acetyl group mono-substituted in the α-position of the acetyl group by a phenyl ring or a heteromonocyclic ring, which group may also bear a substituent to the carbonyl of the acetyl group, for example, phenylacetyl, α-aminophenylacetyl, α-hydroxy-α-phenylacetyl, 2-thienylacetyl, 3-thienylacetyl, 2-furylacetyl, and like groups, wherein the phenyl or heteromonocyclic ring is substituted by hydroxy, protected hydroxy, chloro, bromo, lower alkyl, or methoxy, such as 4-chlorophenylacetyl, 3-hydroxyphenoxyacetyl, 3-hydroxyphenylglycyl, 4-acetoxymandeloyl, and like acyl groups; or an acetoxy group substituted in the α-position by a phenoxy, phenylthio, mono- or disubstituted phenoxy, such as phenoxyacetyl, p-hydroxyphenoxyacetyl, or phenylmercaptoacetyl. The nature of the acyl group, R, is not critical in the present process so long as such an acyl group is less reactive with the halogens bromine and chlorine than the thioalkyl group present at the $C_6$ or $C_7$ position. However, acyl groups having a divalent sulfur atom attached to two aliphatic carbon atoms are generally undesirable as a side chain group of the starting penicillin or cephalosporin ester since such sulfur groups can compete with the 6- and 7-alkylthio groups in the reaction with halogen.

The 6-acylamino-6-alkylthiopenicillanic esters and the 7-acylamino-7-alkylthiocephalosporanic esters, the starting materials in the present process, are prepared according to the process described in Tet. Let. 273 (1973). According to this method, an ester of 6-aminopenicillanic acid (6-APA), 7-aminocephalosporanic acid (7-ACA), or 7-aminodeacetoxycephalosporanic acid (7-ADCA) is reacted with a benzaldehyde, for example, 4-nitrobenzaldehyde, to provide the 6- or 7-benzylideneamino derivative thereof. The imine derivative is then reacted in an inert solvent at a temperature of about −80° to 0°C. with a strong base, such as lithium diisopropyl amide or sodium hydride, to generate the anionic form of the imine which is then reacted with a $C_1$–$C_4$ alkoxycarbonyl-($C_1$–$C_3$ alkyl or benzyl) disulfide, for example, methoxycarbonylmethyl disulfide or ethoxycarbonylbenzyl disulfide, to provide the corresponding 6- or 7-alkylthiolated or benzylthiolated imine. The substituted imine ester is then reacted with a carbonyl reagent, for example, Girard's Reagent T or aminooxyacetic acid to afford the 6-amino-6-alkylthiopenicillanic ester or the 7-amino-7-alkylthiocephalosporanic ester. The alkythio compound is the acylated to provide the starting material for the instant invention. As an example, the 2,2,2-trichloroethyl ester of 7-ACA is reacted with 4-nitrobenzaldehyde in ethanol to afford the trichloroethyl ester of 7-(4-nitrobenzylidene)aminocephalosporanic acid. The imine ester is then reacted with sodium hydride or lithium diisopropylamide to generate the anionic form of the imine, which is reacted with methoxycarbonylmethyl disulfide to provide 2,2,2-trichloroethyl 7-methylthio-7-(4-nitrobenzylidene)aminocephalosporanate. The substituted imine ester is reacted with Girard's Reagent T or other suitable carbonyl reagent, for example, aminooxyacetic acid or phenyl hydrazine, to provide the substituted amino ester, 7-amino-7-methylthiocephalosporanic acid trichloroethyl ester. The free amino nucleus is acylated in a conventional manner to provide the desired 7-acylamido-7-methylthiocephalosporanic acid ester. The foregoing process can provide a wide variety of 6- and 7-alkylthiopenicillins and cephalosporins which can be utilized as starting materials for the present process.

Inert solvents which can be employed in the preparation of the intermediate halosulfonium halides include solvents which are generally unreactive towards the halogens and in which the starting penicillin and cephalosporin esters are at least partially soluble. Solvents which can be employed include benzene, tetrahydrofuran, and chlorinated hydrocarbon solvents, such as, chloroform, methylene dichloride, and tetrachloroethylene. Methylene chloride is a preferred solvent for the process.

One equivalent or a slight excess over one equivalent of halogen is employed in the halogenation of the alkylthio compound. Commonly, a solution of one equivalent of the halogen, chlorine or bromine, in the inert solvent, for example methylene chloride, is added to a solution of the alkylthio compound in methylene chloride or other inert solvent at the reaction temperature of about −80° to −25°C. After the addition of the halogen, the reaction mixture is stirred at −80°C to −25°C for about 10 minutes to insure formation of the sulfonium halide. Thereafter, an excess of an amine, is added to form the desired 6-amino or 7-amino β-lactam compound (and also to serve as hydrogen halide acceptor).

The amines which can be employed in the present process include ammonia, the mono $C_1$–$C_4$ alkyl amines, such as methylamine, ethylamine, n-propylamine, n-butylamine; branched alkyl amines such as isopropylamine, sec-butylamine, and the $C_1$–$C_4$ dialkyl amines such as dimethylamine, methyl-ethylamine, diethylamine, diisobutylamine, and the like.

Following the addition of the amine to the halosulfonium halide which had been formed from the 6-alkylthiopenicillanic ester or 7-alkylthiocephalosporanic ester, the reaction mixture is evaporated to dryness in vacuo at about +10 to −10°C. The reaction product, a 6-amino-6-acylaminopenicillanate or a 7-amino-7-acylaminocephalosporanate, is then recovered from the reaction product mixture by extraction and purified by chromatography. The chromatography is preferably carried out using a silica gel adsorbent.

Following the isolation and purification of the reaction product, the product is reacted by known hydrolysis or hydrogenolysis procedures to effect removal of the ester group to provide the product in free acid form. For example, the benzyl, diphenylmethyl, p-nitrobenzyl, and 3,5-dimethoxybenzyl groups represented by $R_2$ can be removed by hydrogenolysis, for example, by reacting the ester with hydrogen in the presence of 10 percent palladium on carbon catalyst in an inert solvent. The 2,2,2-trichloroethyl group is removed by reacting with zinc and formic or glacial acetic acid. The phenacyl group is removed by hydrolysis with sodium thiophenoxide. Other known carboxylic acid protecting groups which can be employed are removed by known methods.

In cases where $R_2$ is hydrogen, the reaction mixture is concentrated in vacuo at about −10 to +10°C., the product is diluted with water and the mixture is acidified to precipitate the product. For example, the water solution of the product is teated withh 12N hydrochloric acid to adjust the pH from pH 8 to pH 5.

In a preferred embodiment of the present process, a solution of phenacyl 6-phenoxyacetamido-6-methylthiopenicillanate in methylene chloride is cooled to a temperature of about −78°C., and a solution of 1.1 equivalents of chlorine in methylene chloride is added to the cold solution. The reaction is stirred 8–10 minutes to assure formation of the chlorosulfonium chloride at $C_6$, and ammonia is bubbled through the reaction mixture for 1 to 5 minutes. The solvent is removed in vacuo at 0°C. The product, phenacyl 6-amino-6-phenoxyacetamidopenicillanate, is dissolved in ethyl acetate and washed with saturated aqueous sodium chloride solution. After drying of the ethyl acetate solution, the solvent is evaporated, and the product is purified to chromatography. The phenacyl 6-amino-6-phenoxyacetamidopenicillanate is then reacted with sodium thiophenoxide to effect the cleavage of the phenacyl ester group and provide the penicillanic acid.

In carrying out the preparation of the halosulfonium halide intermediate, the preferred halogen is chlorine and the preferred inert solvent is methylene chloride.

Preferred alkylthio and benzylthiopenicillin and cephalosporin starting materials are represented by the following formula

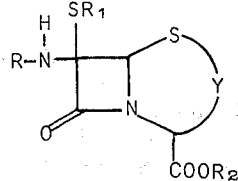

wherein R is $C_1$–$C_7$ alkanoyl, benzoyl, $C_1$–$C_4$ alkylbenzoyl,
halobenzoyl, $C_1$–$C_4$ lower alkoxybenzoyl, nitrobenzoyl,
hydroxybenzoyl, or a group of the formula

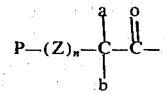

wherein P is phenyl, $C_1$–$C_4$ alkylphenyl, halophenyl, $C_1$–$C_4$ lower alkoxyphenyl, nitrophenyl, hydroxyphenyl, protected hydroxyphenyl or a heteromonocyclic radical containing
O, S, and/or N;
Z is O or S;
$n$ is 0 or 1;
$a$ is hydrogen or $C_1$–$C_3$ alkyl;
$b$ is hydrogen, $C_1$–$C_3$ alkyl, hydroxy, protected hydroxy, amino or protected amino;
$R_1$ and $R_2$ have the same meanings as defined above
Y is

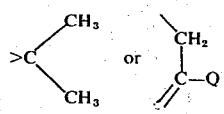

wherein Q is methyl or acetoxymethyl.

With the limitation that when $n$ is one, P is phenyl, $C_1$–$C_4$ alkylphenyl, halophenyl, $C_1$–$C_4$ alkoxyphenyl, nitrophenyl, protected hydroxyphenyl or hydroxyphenyl.

The term "protected amino" refers to an amino group substituted by one of the commonly employed amino blocking groups such as t-butyloxycarbonyl, benzyloxycarbonyl, 2,2,2-trichloroethoxycarbonyl, phthaloyl, 2-iodoethoxycarbonyl and like groups.

The term "protected hydroxy" refers to a hydroxy group substituted by one of the commonly employed hydroxyl blocking groups such as t-butyloxycarbonyl, benzyloxycarbonyl, 2,2,2-trichloroethoxycarbonyl and like groups.

Illustrative of the groups represented by R are the following: phenylacetyl, phenoxyacetyl, benzoyl, 2,6-dimethoxybenzoyl, 4-nitrophenylacetyl, 3-hydroxyphenylacetyl, 4-methylphenoxyacetyl, 2-thienylacetyl, 2-furylacetyl, 3-pyridylacetyl, 2-oxazolylacetyl, 2-thiazolylacetyl, 2,2-dimethylphenylacetyl, mandeloyl, 3-hydroxymandeloyl, phenylglycyl, 4-chlorophenylacetyl, phenylmercaptoacetyl, 2-thienylmercaptoacetyl, 2-pyranylacetyl, 2-pyridylacetyl, 2-oxazolylacetyl, 3-furylacetyl, 2-(1,3,4-thiadiazolyl)acetyl, 4-bromophenylmercaptoacetyl, 2-imidazolylacetyl, 5-pyrimidylacetyl, 3,4-dichlorophenylacetyl, 4-hydroxyphenylmercaptoacetyl, and like acyl groups.

In the foregoing definition the term "$C_1$–$C_7$ alkanoyl" refers to acetyl, propionyl, butyryl, isobutyryl, pivaloyl, valeryl, n-hexanoyl, n-heptanoyl, and like groups. The term "$C_1$–$C_4$ alkyl" has reference to methyl, ethyl, n-propyl, isopropyl, n-butyl, t-butyl, and the like. The term "$C_1$–$C_4$ alkylbenzoyl" refers to 4-methylbenzoyl, 4-isopropylbenzoyl, 4-t-butylbenzoyl, 3,4-dimethylbenzoyl, 3-ethylbenzoyl, 2-methylbenzoyl, and the like; "$C_1$–$C_4$ lower alkoxybenzoyl" refers to 2,6-dimethoxybenzoyl, 4-ethoxybenzoyl, 3-isopropoxybenzoyl, 3-ethoxy-4-methoxybenzoyl, 3,4-dimethoxybenzoyl, and the like; "nitrobenzoyl" refers to 4-nitrobenzoyl, 3-nitrobenzoyl, and the like; "halobenzoyl" is defined herein as the mono or dihalogenated benzoyl groups such as 4-fluorobenzoyl, 3-chlorobenzoyl, 3,4-dichlorobenzoyl, 3-bromobenzoyl, and the like; and "hydroxybenzoyl" refers to such groups as 4-hydroxybenzoyl, 3,4-dihydroxybenzoyl, 2,4-dihydroxybenzoyl, 3-hydroxybenzoyl, and the like.

The term "heteromonocyclic radical containing O, S, and/or N" as employed herein refers to the 5 and 6 membered heterocyclic groups of one ring such as 2-thienyl, 3-thienyl, 2-furyl, 3-furyl, 2-oxazolyl, 2-thiazolyl, triazinyl, tetrazolyl, 2-imidazolyl, 1,3,4-oxadiazolyl, 1,3,4-thiadiazolyl, 2-pyridyl, 3-pyridyl, pyrimidyl, pyrazinyl, 3-pyrryl, pyranyl, piperidyl, and the like.

Representative of the group, -S-$R_1$, are methylthio, ethylthio n-propylthio, isopropylthio, n-butylthio, benzylthio, and the like.

Illustrative of the starting materials which can be employed are the following:

6-[2-(2-furyl)acetamido]-6-methylthiopenicillanic acid,
7-(2-amino-2-phenylacetamido)-7-methylthiodeacetoxycephalosporanic acid,
7-(2-hydroxy-2-phenylacetamido)-7-methylthiocephalosporanic acid,
7-[2-(2-thienyl)acetamido]-7-methylthiocephalosporanic acid,
7-(2-amino-2-phenylacetamido)-7-ethylthiocephalosporanic acid,
7-(2-amino-2-phenylacetamido)-7-ethylthiocephalosporanic acid,
6-(2-phenoxyacetamido)-6-methylthiopenicillanic acid,
6-(2,6-dimethoxybenzamido)-6-methylthiopenicillanic acid,
7-(4-hydroxyphenylacetamido)-7-n-propylthiodeacetoxycephalosporanic acid,
7-(4-chlorophenoxyacetamido)-7-methylthiocephalosporanic acid,
7-phenoxyacetamido-7-isopropylthiocephalosporanic acid,
7-[2-(3-thienyl)acetamido]-7-n-butylthiodeacetoxycephalosporanic acid,
6-(2,2-dimethyl-2-phenylacetamido)-6-methylthiopenicillanic acid,
7-[2-(2-s-triazinyl)acetamido]-7-methylthiodeacetoxycephalosporanic acid,
7-[2-(1,3,4-thiadiazol-2-yl)acetamido]-7-methylthiodeacetoxycephalosporanic acid,
7-[2-(1,3,4-oxadiazol-2-yl)acetamido]-7-ethylthiocephalosporanic acid,
6-[2-amino-2-(4-hydroxyphenyl)acetamido]-6-isopropylthiopenicillanic acid,
7-acetamido-7-benzylthiocephalosporanic acid,
7-(2-pyranylacetamido)-7-methylthiocephalosporanic acid,
7-(2-piperidylacetamido)-7-methylthiodeacetoxycephalosporanic acid,
7-(5-oxazolylacetamido)-7-methylthiodeacetoxycephalosporanic acid,
6-phenylacetamido-6-methylthiopenicillanic acid,
7-phenoxyacetamido-7-methylthiodeacetoxycephalosporanic acid, and the like.

The halosulfonium salts prepared in the first step of the present process are relatively stable substances under the conditions described above for their preparation. In the present process, however, it is preferable to prepare and react the sulfonium halides in situ.

In the naming of the halosulfonium halides herein, abbreviated nomenclature is used for convenience. The group

is referred to as a haloalkylsulfonio substituent at the $C_6$ of a penicillin compound or at the $C_7$ of a cephalosporin compound. Accordingly, the compound represented by the formula

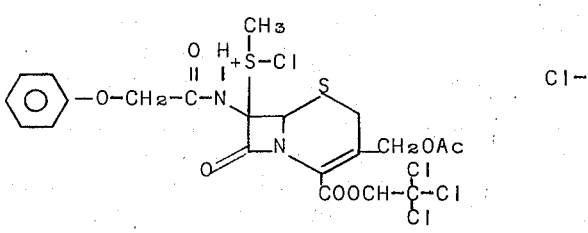

is named herein as 2,2,2-trichloroethyl 7-phenoxyacetamido-7-chloromethylsulfoniocephalosporanate chloride.

The following exemplary halosulfonium halides are useful as intermediates for preparing the corresponding amino compounds and are named according to the abbreviated system described above:

2,2,2-trichloroethyl 6-phenylacetamido-6-chloromethylsulfoniopenicillanate chloride, p-nitrobenzyl 6-phenoxyacetamido-6-bromomethylsulfoniopenicillanate bromide, 2,2,2-trichloroethyl-6-[2-(2-thienyl)acetamido]-6-chloromethylsulfoniopenicillanate chloride, benzyl 6-acetamido-6-chloroethylsulfoniopenicillanate chloride, phenacyl 6-phenoxyacetamido-6-chloromethylsulfoniopenicillanate chloride, 2,2,2-trichloroethyl 7-phenoxyacetamido-7-chloromethylsulfoniocephalosporanate chloride, 2,2,2-trichloroethyl 7-[2-(2-thienyl)-acetamido]-7-chloromethylsulfoniodeacetoxycephalosporanate chloride, p-nitrobenzyl 7-phenoxyacetamido-7-chloroisopropylsulfoniodeacetoxycephalosporanate chloride, diphenylmethyl 7-[2-(2-thienyl)acetamido]-7-chloromethylsulfoniocephalosporanate chloride, p-nitrobenzyl 6-(2,6-dimethoxybenzamido)-6-bromomethylsulfoniopenicillanate bromide, 2,2,2-trichloroethyl 7-(2-hydroxyphenylacetamido)-7-chloroethylsulfoniodeacetoxycephalosporanate chloride, 2,2,2-trichloroethyl 7-(2-aminophenylacetamido)-7-chlorobenzylsulfoniodeacetoxycephalosporanate chloride, p-nitrobenzyl 6-acetamido-6-(chloro-n-propylsulfonio)penicillanate chloride, 2,2,2-trichlorethyl 6-acetamido-6-bromoethylsulfoniopenicillanate chloride, 2,2,2-trichloroethyl 7-acetamido-7-bromoethylsulfoniocephalosporanate bromide and like penicillin and cephalosporin sulfonium halide esters.

Representatives of the compounds provided in this invention are the following:

6-acetamido-6-methylaminopenicillanic acid,
6-propionamido-6-dimethylaminopenicillanic acid,
6-phenoxyacetamido-6-aminopenicillanic acid,
6-phenylacetamido-6-n-butylaminopenicillanic acid,
6-phenoxyacetamido-6-diisopropylaminopenicillanic acid,
6-[2-(2-thienyl)acetamido]-6-aminopenicillanic acid,
6-phenylacetamido-6-ethylaminopenicillanic acid,
6-phenoxyacetamido-6-diethylaminopenillanic acid,
6-[2-hydroxy-2-(phenylacetamido)]-6-aminopenicillanic acid,
6-[2-amino-2-(phenylacetamido]-6-methylaminopenicillanic acid,
6-[2-(3-thienyl)acetamido]-6-aminopenicillanic acid,
6-(2,6-dimethoxybenzamido)-6-aminopenicillanic acid,
6-benzamido-6-di-n-propylaminopenicillanic acid,
6-(4-hydroxybenzamido)-6-methylaminopenicillanic acid,
7-acetamido-7-aminocephalosporanic acid,
7-propionamido-7-methylaminocephalosporanic acid,
7-valeramido-7-aminodeacetoxycephalosporanic acid,
7-valeramido-7-methylaminocephalosporanic acid,
7-benzamido-7-diethylaminodeacetoxycephalosporanic acid,
7-benzamido-7-aminodeacetoxycephalosporanic acid,
7-(2,6-dimethoxybenzamido)-7-diisopropylaminodeacetoxycephalosporanic acid,
7-phenylacetamido-7-n-butylaminocephalosporanic acid,
7-p-chlorophenylacetamido-7-n-propylaminodeacetoxycephalosporanic acid,
7-p-nitrophenylacetamido-7-diethylaminodeacetoxycephalosporanic acid,
7-phenoxyacetamido-7-diisobutylaminocephalosporanic acid,
7-phenoxyacetamido-7-ethylaminocephalosporanic acid,
7-[2-(2-thienyl)acetamido]-7-aminocephalosporanic acid,
7-[2-(2-thienyl)acetamido]-7-dimethylaminocephalosporanic acid,
7-[2-(3-thienyl)acetamido]-7-sec-butylaminodeacetoxycephalosporanic acid,
7-chloroacetamido-7-t-butylaminodeacetoxycephalosporanic acid,
7-(2-pyranylacetamido)-7-aminodeacetoxycephalosporanic acid,
7-[2-(oxazol-2-yl)acetamido[-7-methylaminocephalosporanic acid,
7-[2-(1,3,4-thiadiazo-2-yl)acetamido]-7diisopropylaminodeacetoxycephalosporanic acid,
7-[2-(2-pyridyl)acetamido]-7-dimethylaminodeacetoxycephalosporanic acid,
7-[2-(2-pyrryl)acetamido]-7-aminodeacetoxycephalosporanic acid,
7-(3-isopropoxybenzoylacetamido)-7-aminodeacetoxycephalosporanic acid,
7-(4-hydroxyphenoxyacetamido)-7-aminodeacetoxycephalosporanic acid,
7-[2-(carbobenzoxyamino)acetamido]-7-dimethylaminocephalosporanic acid,
6-[2-(2,2,2-trichloroethoxycarbonyloxy)acetamido]-6-methylethylaminopenicillanic acid,
7-[2-(oxazol-2-yl)acetamido]-7-di-n-propylaminocephalosporanic acid,
7-[2-(tetrazol-2-yl)acetamido]-7-aminodeacetoxycephalosporanic acid,
7-phenylmercaptoacetamido-7-methylaminodeacetoxycephalosporanic acid,
7-(2-aminophenylacetamido)-7-aminodeacetoxycephalosporanic acid,
7-(2-aminophenylacetamido)-7-diethylaminodeacetoxycephalosporanic acid, and like penicillanic, cephalosporanic acids, the carboxylic acid protecting ester derivatives thereof, and the pharmaceutically acceptable salts thereof.

The esters of the novel compounds described herein can be converted to the corresponding novel carboxylic acids which possess antibiotic activity and are useful in combating infections due to gram positive and gram negative organisms. Accordingly, the products of the present invention can be parenterally administered in a suitable non-toxic dose to an infected host in the treatment of such infections. In general, the compounds can be administered to a dose between about 50 and 500 mg./kg. of body weight. Substantial variation in the dosage regimen may be required depending on such conditions as the general physical condition of the host, the severity of the infection, the locus of the infection and the particular organism responsible for the infection. For example, a single daily dose may suffice with a particular host while with others, multiple doses spaced throughout the day may be required to achieve the desired response.

The following detailed examples further illustrate the present invention.

A. Conversion of Alkylthio Compounds to Amines

EXAMPLE 1

Phenacyl 6-phenoxacetamido-6-aminopenicillanate

To a solution of 0.687 g. of phenacyl 6-phenoxyacetamido-6-methylthiopenicillante in 60 ml. of methylene chloride at −78°C. is added a solution of 20 ml. of methylene chloride containing 0.12 g. of chlorine. Addition is completed over 3 minutes, then ammonia gas is bubbled through the solution for approximately one minute. The solvent is removed in vacuo by immersing the flask in an ice bath and employing a rotating evaporator.

The crude product residue is dissolved in ethyl acetate and washed with aqueous saturated sodium chloride solution. After drying, the product is concentrated in vacuo yielding 0.582 g. of product which is applied to preparative silica gel plates. A solvent system of 25 percent hexane in ethyl acetate is used, and 142 mg. of the phenacyl 6-phenoxyacetamido-6-aminopenicillanate is obtained and identified by its nuclear magnetic resonance spectrum.

EXAMPLE 2

6-Phenoxyacetamido-6-aminopenicillanic acid

To a solution of 0.310 g. of 6-phenoxyacetamido-6-methylthiopenicillanic acid in 60 ml. of methylene chloride at −78°C. is added a solution of 0.078 g. of chlorine in 20 ml. of methylene chloride over a 3 minute interval. After approximately 8 minutes, ammonia gas is bubbled into the solution for 5 minutes. The solvent is removed in vacuo using a rotary evaporator. The residue is dissolved in 10 ml. of water and 12N hydrochloric acid added to change the pH from pH 8 to pH 5. A precipitate results. The liquid is decanted and the precipitate is washed with water and ether yielding 70 mg. of 6-phenoxyacetamido-6-aminopenicillanic acid. The water from the washing of the product is adjusted to pH 2 and extracted with ethyl acetate. Concentration in vacuo yields an additional small quantity of material.

EXAMPLE 3

2,2,2-Trichlorethyl 6-phenoxyacetamido-6-diisopropylaminopenicillanate

Following the reaction conditions described in Example 1, 475 mg. of 2,2,2-trichloroethyl 6-phenoxyacetamido-6-thiomethylpenicillanate is reacted with chlorine and the intermediate chloromethylsulfonium chloride is treated with diisopropylamine to provide, after evaporation, extraction and preparative thin layer chromatography, 99 mg. of 2,2,2-trichloroethyl 6-phenoxyacetamido-6-diisopropylaminopenicillanate.

EXAMPLE 4 p-Nitrobenzyl 7-dimethylamino-7-[2-(thienyl)acetamido]deacetoxycephalosporanate

Following the procedures described in Example 1, p-nitrobenzyl 7-[2-(2-thienylacetamido)]-7-thiomethylcephalosporante is reacted with one equivalent of chlorine at −78°C. in methylene chloride to provide p-nitrobenzyl 7-[2-(2-thienyl)-acetamido)]-7-chloromethylsulfoniodeacetoxycephalosporanate. Three equivalents of dimethylamine in methylene chloride are added, and after 5 minutes the solvent is evaporated in vacuo to provide p-nitrobenzyl 7-dimethylamino-7-[2-(2-thienyl)acetamido]deacetoxycephalosporanate.

EXAMPLE 5

7-Phenoxyacetamido-7-ethylaminocephalosporanic acid

Following the procedure described in Example 2, 7-phenoxyacetamido-7-benzylthiocephalosporanic acid is reacted at −78°C. with one equivalent of bromine in methylene chloride to provide 7-phenoxyacetamido-7-bromobenzylsulfoniocephalosporanic acid. The solution was treated with 2.5 equivalents of ethylamine in methylene chloride. Isolation as in Example 2 yielded the 7-phenoxyacetamido-7-ethylaminocephalosporanic acid.

EXAMPLE 6

2,2,2-Trichloroethyl 7-p-chlorophenylacetamido-7-n-propylaminodeacetoxycephalosporanate Following the procedure described in Example 1, 2,2,2-trichloroethyl 7-p-chlorophenylacetamido-7-methylthiodeacetoxycephalosporanate is reacted with one equivalent of chlorine in methylene chloride at −78°C. to provide 2,2,2-trichloroethyl 7-p-chlorophenyl-7-chloromethylsulfoniodeacetoxycephalosporanate; then the solution is treated with 2.1 equivalents of n-propylamine in methylene chloride. After the solution is added and the reaction stirred 5 minutes, the solvent is removed in vacuo and the product extracted, washed, and reconcentrated. Preparative thin layer chromatography provides the 2,2,2-trichloroethyl 7-p-chlorophenylacetamido-7-n-propylaminodeacetoxycephalosporante.

B. Conversion of Esters to Acids

EXAMPLE 7

6-Phenoxyacetamido-6-aminopenicillanic acid

The product from Example 1 is dissolved in a mixture of 3 ml. of DMF containing 0.0392 g. of sodium thiophenoxide at 0°C., and the reaction is stirred 5 minutes. Approximately 50 ml. of ether is added to precipitate the 6-phenoxyacetamido-6-aminopenicillanic acid. The liquid is decanted from the precipitate, and the solid is triturated with ether and filtered, yielding 53 mg. of product.

EXAMPLE 8

6-Phenoxyacetamido-6-diisopropylaminopenicillanic acid

The trichloroethyl ester from Example 3 is reacted with a suspension of zinc (5 gram-atom excess) in 90 percent formic acid at a temperature of about 25°C., and the reaction is diluted with brine. The diluted mixture is extracted with ethyl acetate, and the extract is washed with dilute sodium bicarbonate, water, and is dried. The dried extract is evaporated to dryness to provide 6-phenoxyacetamido-6-diisopropylaminopenicillanic acid sodium salt. The salt is dissolved in a mixture of water and ethyl acetate and the solution is acidified with dilute hydrochloric acid. The ethyl acetate layer is separated, washed with water and dried. The extract is evaporated to dryness to provide 6-phenoxyacetamido-6-diisopropylaminopenicillanic acid.

EXAMPLE 9

7-Dimethylamino-7-[2-(2-thienyl)acetamido]-deacetoxycephalosporanate

The p-nitrobenzyl ester from Example 4 is dissolved in ethanol and 10 percent (by weight of the ester) of 5 percent palladium on carbon is added. A hydrogen pressure only slightly greater than one atmosphere achieves complete deesterification in 12 hours. Filtering of catalyst and concentrating of the solvent in vacuo yields the 7-dimethylamino-7-[2-(2-thienyl)acetamido]deacetoxycephalosporanate.

We claim:

1. The process for preparing a compound of the formula

13

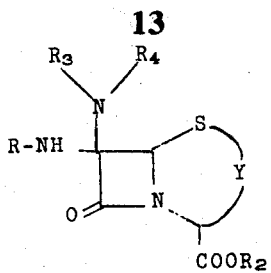

which comprises the steps of: (a) reacting in an inert solvent an alkylthio compound of the formula

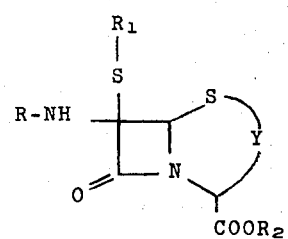

with chlorine, bromine, or sulfuryl chloride at a temperature between −80° and −25°C. to form the β-lactam halosulfonium halide of the formula

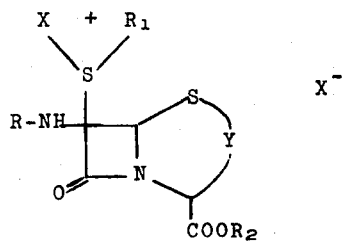

14 and (b) reacting said β-lactam halosulfonium halide in an inert solvent with an excess of an amine $R_3R_4NH$; wherein the formulas above R is hydrogen, $C_1$–$C_7$ alkanoyl, benzoyl, $C_1$–$C_4$ alkylbenzoyl, halobenzoyl, $C_1$–$C_4$ alkoxybenzoyl, nitrobenzoyl, hydroxybenzoyl, or a group of the formula

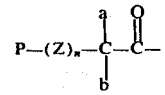

wherein P is phenyl, $C_1$–$C_4$ alkylphenyl, $C_1$–$C_4$ alkoxyphenyl, halophenyl, nitrophenyl, hydroxyphenyl, protected hydroxyphenyl or a heteromonocyclic radical containing O, S, and/or N;

Z is O or S;

n is 0 or 1;

a is hydrogen or $C_1$–$C_3$ alkyl;

b is hydrogen, $C_1$–$C_3$ alkyl, hydroxy, protected hydroxy, amino, or protected amino;

$R_1$ is $C_1$–$C_3$ alkyl or benzyl;

$R_2$ is hydrogen or a carboxylic acid protecting ester forming group;

$R_3$ and $R_4$ are hydrogen or $C_1$–$C_4$ alkyl;

X is chloro or bromo; and

Y is

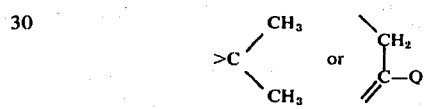

wherein Q is methyl or acetoxymethyl, with the limitation that when n is 1, P is phenyl, $C_1$–$C_4$ alkylphenyl, $C_1$–$C_4$ alkoxyphenyl, nitrophenyl, hydroxyphenyl or protected hydroxyphenyl.

* * * * *